US010470784B2

(12) United States Patent
Mottola et al.

(10) Patent No.: US 10,470,784 B2
(45) Date of Patent: Nov. 12, 2019

(54) MEDICAL GRASPING DEVICE

(71) Applicant: Merit Medical Systems, Inc., South Jordan, UT (US)

(72) Inventors: Jim Mottola, Salt Lake City, UT (US); Peter Sutcliffe, Palm Coast, FL (US); F. Mark Ferguson, Salt Lake City, UT (US); Nate Shirley, Pleasant Grove, UT (US); Richard P. Jenkins, Bluffdale, UT (US); Christopher Cindrich, Draper, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 221 days.

(21) Appl. No.: 14/955,623

(22) Filed: Dec. 1, 2015

(65) Prior Publication Data
US 2016/0151083 A1 Jun. 2, 2016

Related U.S. Application Data
(60) Provisional application No. 62/086,432, filed on Dec. 2, 2014.

(51) Int. Cl.
*A61B 17/22* (2006.01)
*A61B 17/30* (2006.01)

(52) U.S. Cl.
CPC ............ *A61B 17/22031* (2013.01); *A61B 2017/22035* (2013.01); *A61B 2017/305* (2013.01)

(58) Field of Classification Search
CPC ... A61B 17/22031; A61B 17/29; A61B 17/30; A61B 2017/22035; A61B 2017/2926; A61B 2017/2945; A61B 2017/301
See application file for complete search history.

(56) References Cited

U.S. PATENT DOCUMENTS

| | | | |
|---|---|---|---|
| 5,222,973 A * | 6/1993 | Sharpe | A61B 17/29 294/100 |
| 5,226,908 A | 7/1993 | Yoon | |
| 5,653,716 A * | 8/1997 | Malo | A61B 17/0483 606/110 |
| 6,361,540 B1 * | 3/2002 | Gauderer | A61B 17/221 606/106 |
| 6,416,519 B1 | 7/2002 | Vandusseldorp | |
| 6,679,893 B1 | 1/2004 | Tran | |
| 7,824,407 B2 * | 11/2010 | Yamamoto | A61B 18/1445 606/46 |

(Continued)

FOREIGN PATENT DOCUMENTS

WO 199522932 8/1995

OTHER PUBLICATIONS

International Search Report and Written Opinion dated Apr. 22, 2016 for PCT/US2015/063179.

(Continued)

*Primary Examiner* — Sarah A Simpson
(74) *Attorney, Agent, or Firm* — Stoel Rives LLP

(57) ABSTRACT

A medical grasping device is disclosed. The medical grasping device may be configured to retrieve an object from within a body lumen. A medical grasping device assembly, wherein a portion of the medical grasping device is disposed within a lumen of a delivery sheath, and methods of using the medical grasping device assembly are also disclosed.

18 Claims, 7 Drawing Sheets

(56) References Cited

U.S. PATENT DOCUMENTS

| | | | |
|---|---|---|---|
| 8,080,053 B2* | 12/2011 | Satasiya | A61F 2/91 623/1.15 |
| 2002/0143387 A1 | 10/2002 | Soetikno et al. | |
| 2003/0212429 A1* | 11/2003 | Keegan | A61F 2/01 606/200 |
| 2007/0186933 A1* | 8/2007 | Domingo | A61B 17/12022 128/207.15 |
| 2008/0269774 A1 | 10/2008 | Garcia et al. | |
| 2013/0046334 A1* | 2/2013 | Jones | A61B 17/22031 606/200 |
| 2014/0142609 A1 | 5/2014 | Keegan et al. | |

OTHER PUBLICATIONS

"Essential Foreign Body Equipment", Gastrointestinal Endoscopy, Jun. 2011. http://wwwusendoscopy.com/~/media/Files/Documents/Checklist/760449FFBchecklist8511.pdf downloaded from the internet Apr. 15, 2016.

"Raptor Grasping Device", US Endoscopy, Jun. 2012. http://www.usendoscopy.com/~/media/Files/Documents/IFU/00731747E_ifu%20%20711177%20Oraptor%20grasping%20devies.pdf downloaded from the internet Apr. 15, 2016.

"Talon Grasping Device", US Endoscopy, Sep. 2013. http://www.usendoscopy.com/~/media/Files/Documents/OFU/00731998B_IFU%20711175%20Talon%20grasping%20device.pdf downloaded from the internet Apr. 15, 2016.

"Technical Status Evaluation Report: Endoscopic Retrieval Devices", Gastrointestinal Endoscopy, vol. 69 No. 6, 2009. http://www.asge.org/uploadedFiles/Publications_and_Products_Guidelines/Endo%20retreval.pdf downloaded from the internet Apr. 15, 2016.

Huang, et al., "Intentional Swallowing of Foreign Bodies is a Recurrent and Costly Problem that Rarely Causes Engoscopy Complications", Clinical Gastroenterology and Hepatology,8, 2010, 941-946. http://www.cghjournal.org/article/S1542-3565(10)00736-6/pdf downloaded from the internet Apr. 15, 2016.

Extended European Search Report dated May 9, 2018 for EP15866067.0.

European Search Report dated Apr. 15, 2019 for EP15866067.0.

* cited by examiner

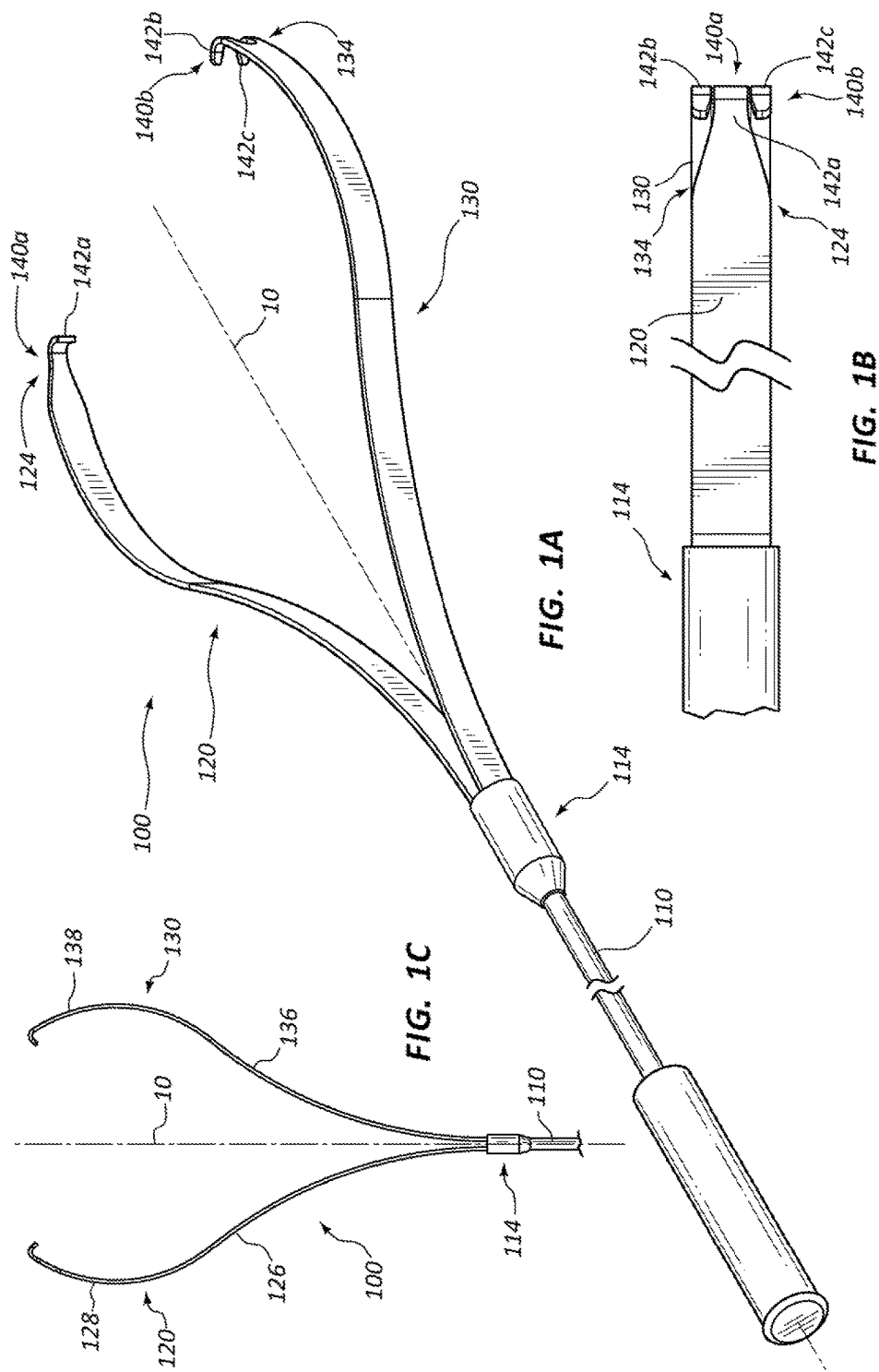

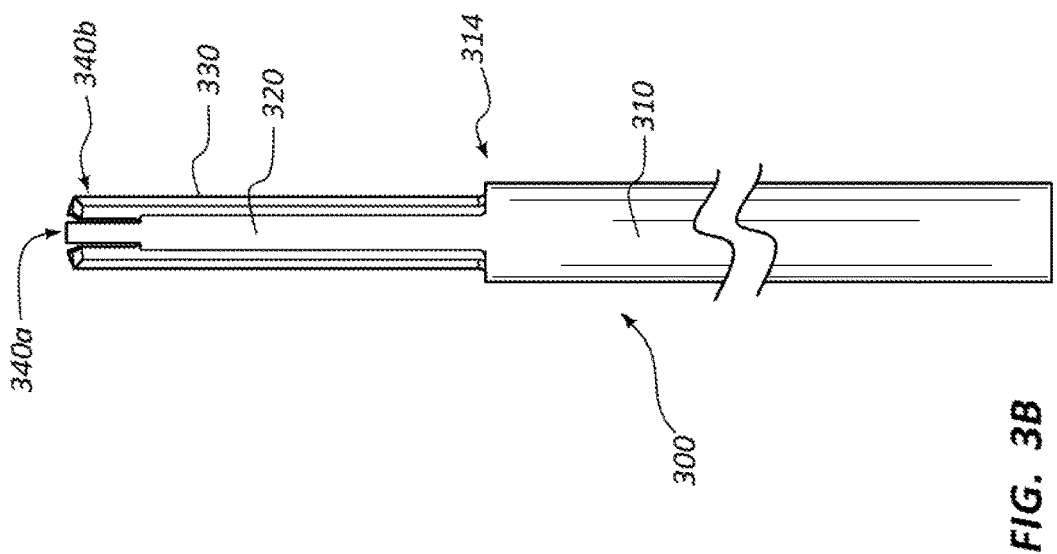
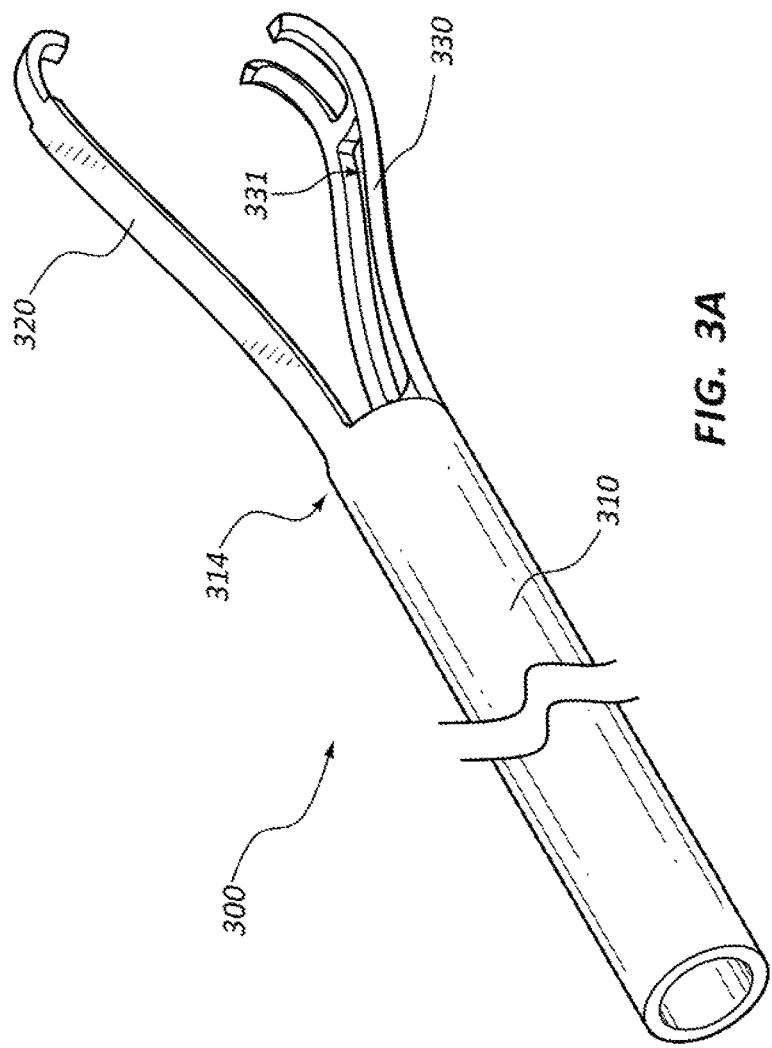

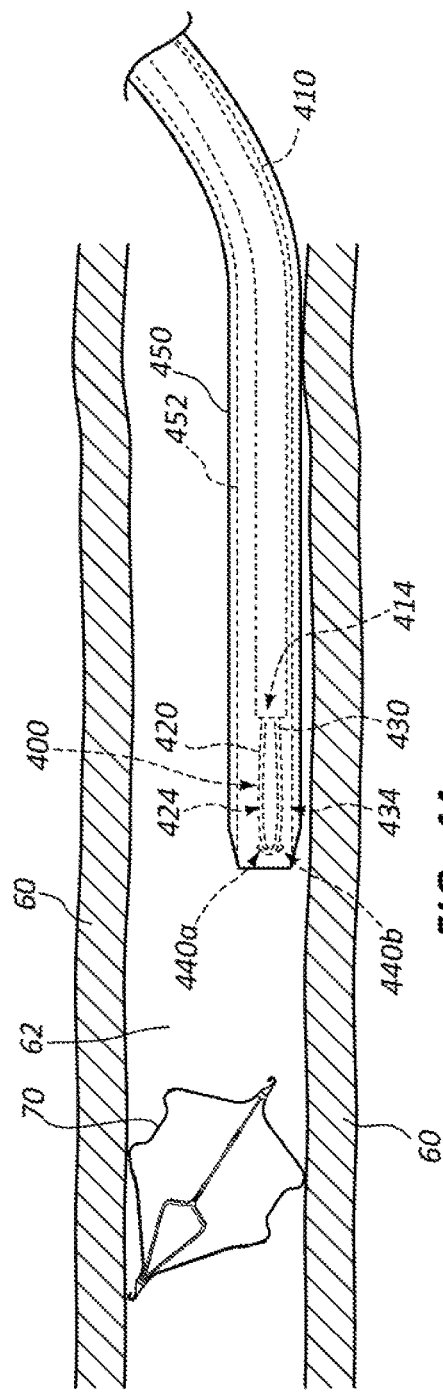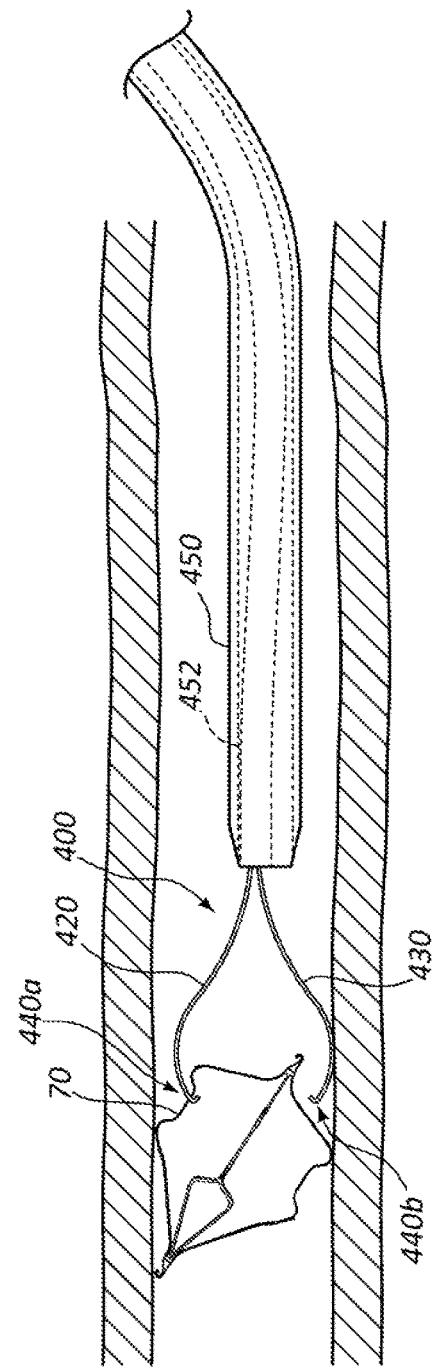
FIG. 4A
FIG. 4B

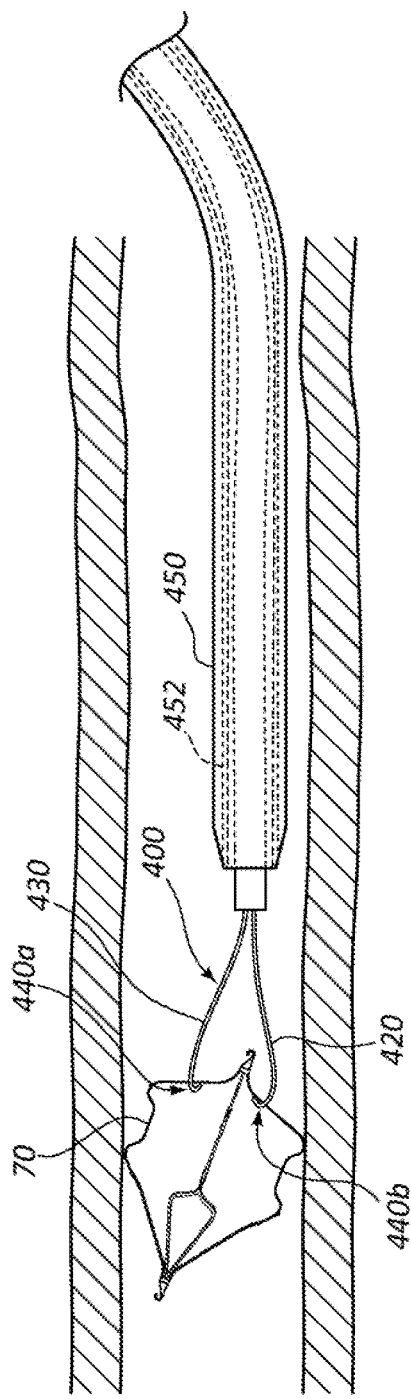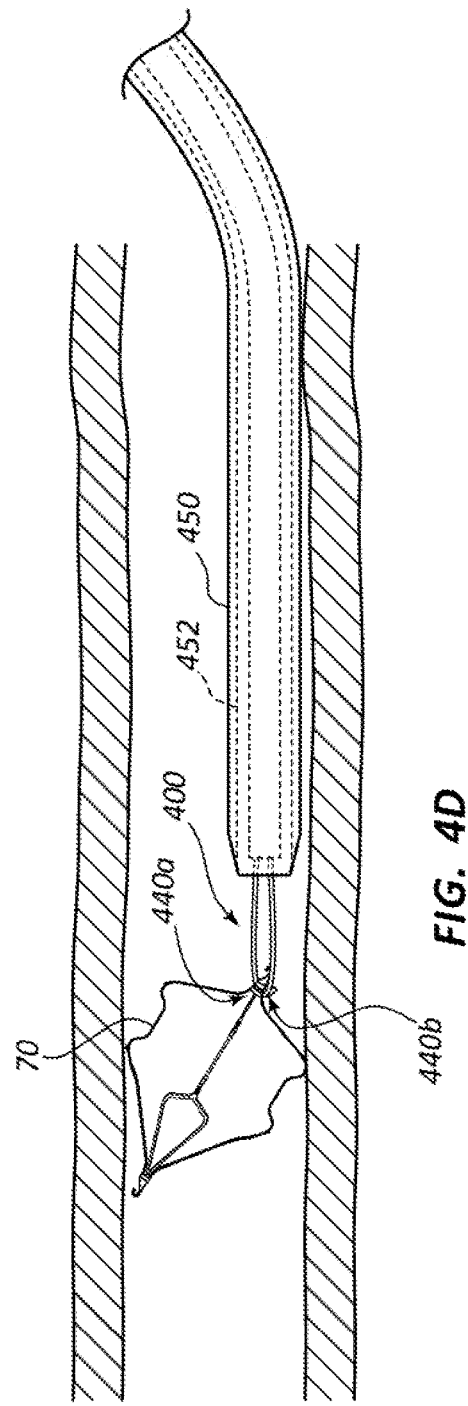

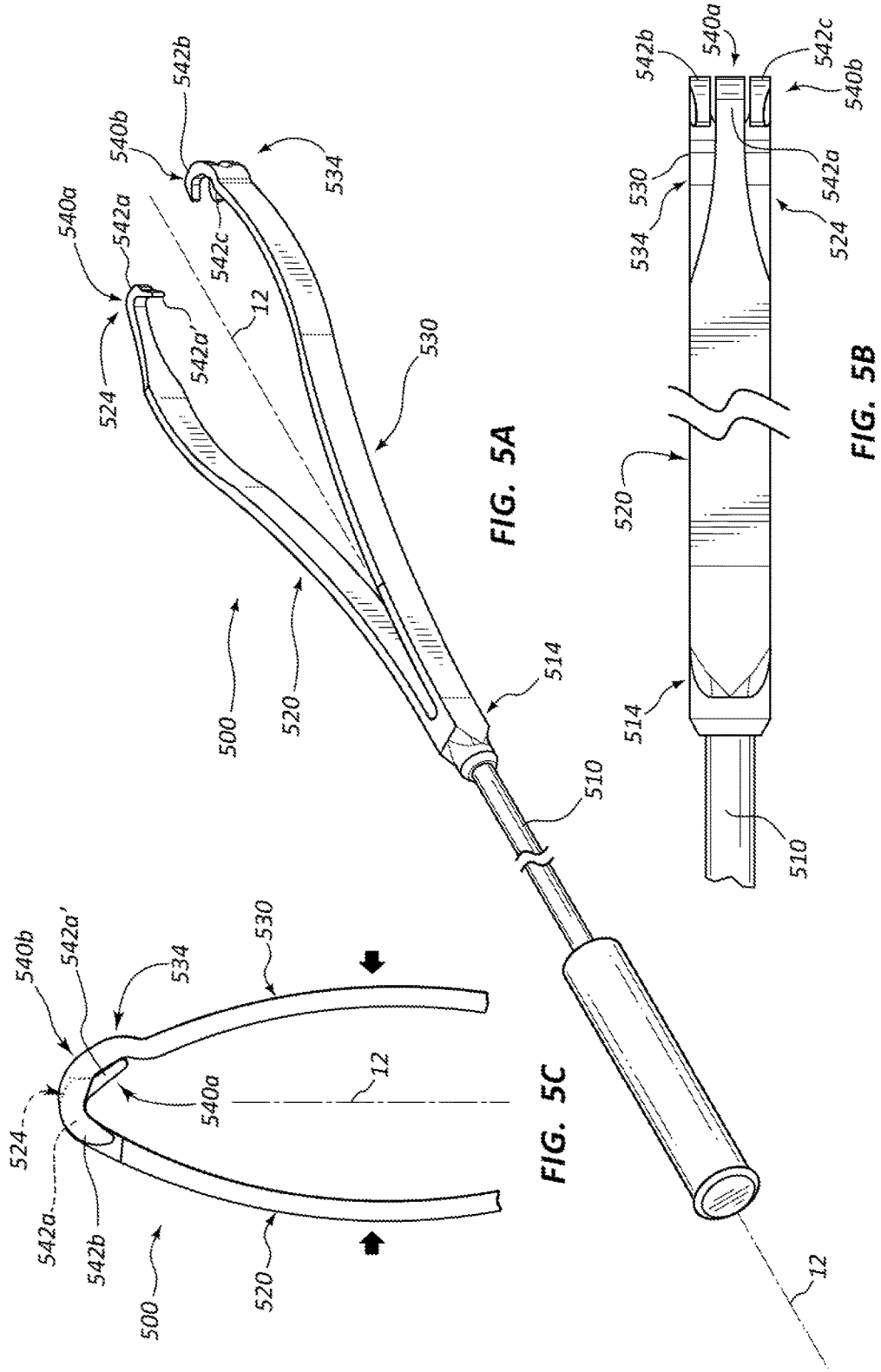

MEDICAL GRASPING DEVICE

RELATED APPLICATIONS

This application claims priority to U.S. Provisional Application No. 62/086,432 filed on Dec. 2, 2014 and titled, "Medical Grasping Device" which is hereby incorporated by reference in its entirety.

TECHNICAL FIELD

The present disclosure relates generally to medical grasping devices. More specifically, the present disclosure relates to medical grasping devices configured for retrieval of objects from body lumens and methods of use.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

FIG. 1A is a perspective view of an embodiment of a medical grasping device.

FIG. 1B is a side view of a portion of the medical grasping device of FIG. 1A.

FIG. 1C is a front view of a portion of the medical grasping device of FIG. 1A.

FIG. 3A is a perspective view of yet another embodiment of a medical grasping device.

FIG. 3B is a side view of the medical grasping device of FIG. 3A.

FIG. 4A is a side view of an embodiment of a medical grasping device assembly disposed in a body lumen.

FIG. 4B is a side view of the medical grasping device assembly of FIG. 4A wherein resilient prongs of the medical grasping device are partially distally displaced from within a lumen of a delivery sheath.

FIG. 4C is a side view of the medical grasping device assembly of FIG. 4A wherein the resilient prongs of the medical grasping device are fully distally displaced from within the lumen of the delivery sheath.

FIG. 4D is a side view of the medical grasping device assembly of FIG. 4A wherein the medical grasping device has secured a vascular filter.

FIG. 5A is a perspective view of another embodiment of a medical grasping device in an open configuration.

FIG. 5B is a side view of a portion of the medical grasping device of FIG. 5A.

FIG. 5C is a front view of a portion of the medical grasping device of FIG. 5A in a closed configuration.

DETAILED DESCRIPTION

Figure 2A:
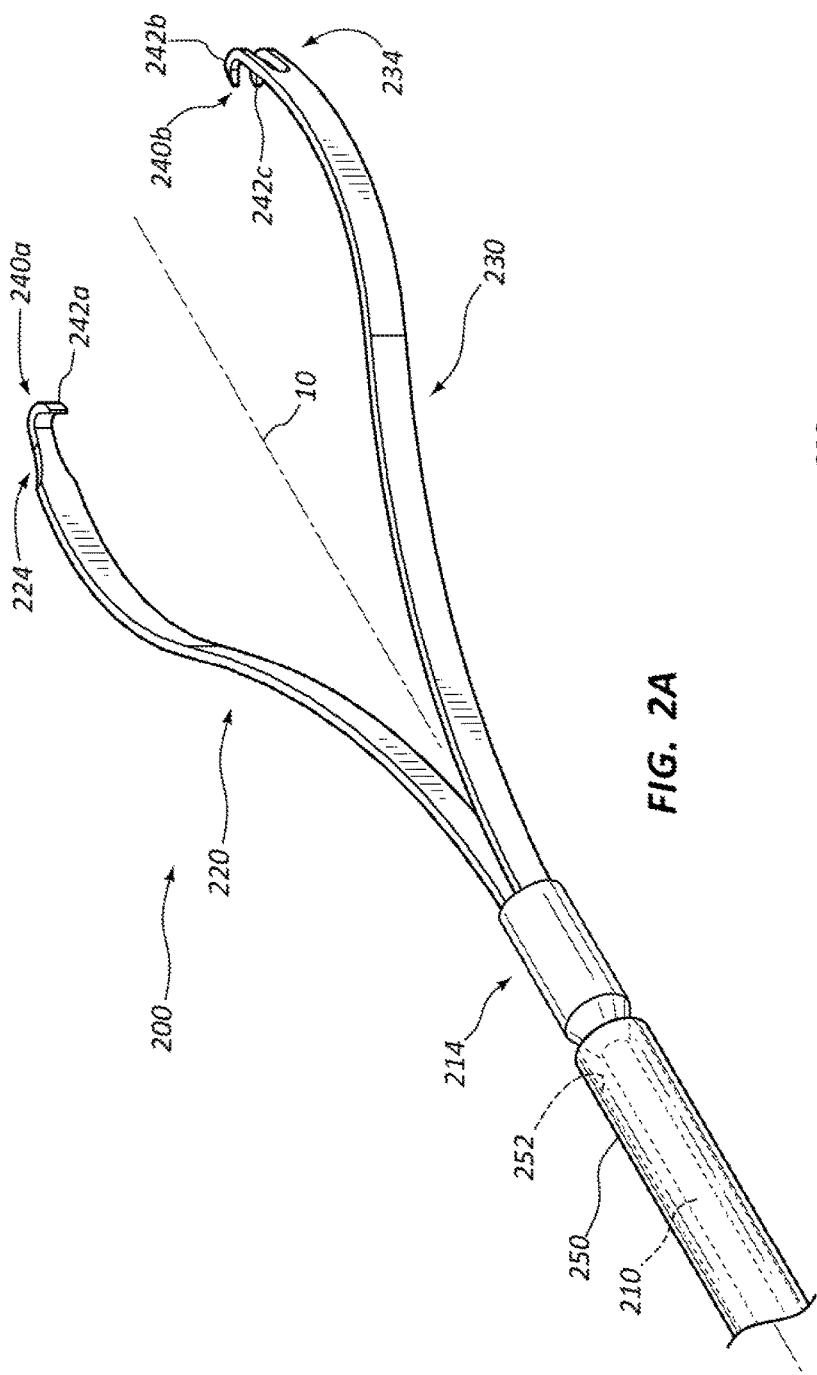
FIG. 2A is a perspective view of another embodiment of a medical grasping device.

The various embodiments disclosed herein generally relate to medical grasping devices. More specifically, the various embodiments relate to medical grasping device systems, for example, medical grasping device assemblies and related methods. In some embodiments, the medical grasping device assembly comprises an elongate member, a plurality of resilient prongs, and a delivery sheath. Also disclosed herein are methods of utilizing a medical grasping device assembly.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a medical grasping device is defined as the end closest to the practitioner during insertion or utilization of the medical grasping device. The distal end is the end opposite the proximal end, along the longitudinal direction of the medical grasping device.

The terms "foreign body" and "foreign object" refer to any item, matter, or substance, such as a medical device or an embolism, which may be disposed or positioned within a body lumen. In some embodiments, the foreign body or object may be undesirable or unwanted. Specifically, a foreign body or object may be an item that a practitioner desires or targets to remove or retrieve from within a body lumen. For example, the foreign body or object may comprise a medical device (e.g., a vascular filter or a stent) that is disposed within a vessel, and a medical grasping device of the present disclosure may be configured to retrieve the medical device from within the vessel. Further, disclosure herein relating to displacement of foreign objects may analogously be applied to any target for displacement or removal, including, for example, bodily structures or materials.

The term "resilient" refers to a component, device, or object that is formed with a particular shape, that can then be elastically deformed into a different shape, but that can return to the original shape when unconstrained. For example, a resilient prong may be formed with a first shape, the resilient prong may then be constrained (i.e., disposed within a lumen of a sheath) to elastically deform it into a second shape, then unconstrained (i.e., displaced out of the lumen of the sheath) such that the resilient prong returns to its first shape. Shape memory alloys, including NITINOL, are examples of resilient materials.

FIG. 1A illustrates an embodiment of a medical grasping device 100. As depicted, the medical grasping device 100 can comprise an elongate member 110. The medical grasping device 100 may also comprise at least two resilient prongs 120, 130. In the illustrated embodiment, the medical grasping device 100 comprises a first resilient prong 120 and a second resilient prong 130. In other embodiments, the medical grasping device 100 may comprise three resilient prongs, four resilient prongs, or more resilient prongs. The first and second resilient prongs 120, 130 are coupled to the elongate member 110 at a distal end 114 of the elongate member 110, and each of the first and second resilient prongs 120, 130 can extend distally from the distal end 114 of the elongate member 110.

At least one engagement feature 140a may be disposed at a distal end 124 of the first resilient prong 120. Likewise, at least one engagement feature 140b may be disposed at a distal end 134 of the second resilient prong 130. In the illustrated embodiment, the engagement feature 140a comprises one curved portion 142a, wherein the curved portion 142a is disposed at the distal end 124 of the first resilient prong 120. Also, as illustrated, the engagement feature 140b comprises two curved portions 142b, 142c, wherein the two curved portions 142b, 142c are disposed at the distal end 134 of the second resilient prong 130. The one curved portion 142a of the first resilient prong 120 may be configured to interlock or engage with the two curved portions 142b, 142c of the second resilient prong 130 when the distal ends 124, 134 of the first and second resilient prongs 120, 130, respectively, are displaced toward each other (as discussed in further detail below). The interlocking of the curved portions 142a, 142b, 142c may be configured to secure a target foreign object disposed within a body lumen. For example, a target foreign object may be secured before any force is applied on the target foreign object by a medical grasping device. Such a configuration may facilitate a traumatic, or less traumatic, securement of the target foreign object prior to displacement of the target foreign object.

Other configurations of engagement features are also contemplated. For example, the engagement features may comprise one or more L-shaped portions (i.e., portions that are not substantially curved). In another example, a first engagement feature may comprise two teeth or projections separated by a gap or slot and a second engagement feature, which is configured to interlock with the first engagement feature, wherein the second engagement feature may comprise a single tooth or projection configured to be disposed, at least partially, within the gap or slot of the first engagement feature.

With continued reference to FIG. 1A, each of the first resilient prong 120 and the second resilient prong 130 curves outwardly from an extension of a longitudinal axis 10 of the elongate member 110. In contrast, each of the curved portions 142a, 142b, 142c curves inwardly toward the extension of the longitudinal axis 10 of the elongate member 110.

As depicted, each of the first resilient prong 120 and the second resilient prong 130 extends from the distal end 114 of the elongate member 110 such that the first resilient prong 120 extends in a substantially opposite direction from the second resilient prong 130. Stated another way, the extension of the first resilient prong 120 from the elongate member 110 generates or forms a substantially mirror image of the extension of the second resilient prong 130 from the elongate member 110, and vice versa. As illustrated, the first resilient prong 120 extends from a first portion at the distal end 114 of the elongate member 110 and the second resilient prong 130 extends from a second portion at the distal end 114 of the elongate member 110, wherein the first position and the second position are disposed at substantially opposite positions along a circumference of the distal end 114 of the elongate member 110. As such, each of the first resilient prong 120 and the second resilient prong 130 is substantially disposed within a single plane. Other dispositions of the first and second resilient prongs 120, 130 around the circumference of the distal end 114 of the elongate member are also within the scope of this disclosure.

FIG. 1B is a side view of a portion of the medical grasping device 100 of FIG. 1A. In the illustrated embodiment, the relative position of the first resilient prong 120 in relation to the position of the second resilient prong 130 is shown. As described above, at least one engagement feature 140a can be disposed at the distal end 124 of the first resilient prong 120. Likewise, at least one engagement feature 140b may be disposed at the distal end 134 of the second resilient prong 130. The engagement feature 140a of the first resilient prong 120, as illustrated, comprises one curved portion 142a, wherein the curved portion 142a is disposed at the distal end 124 of the first resilient prong 120. The engagement feature 140b of the second resilient prong 130 comprises two curved portions 142b, 142c, wherein the curved portions 142b, 142c are disposed at the distal end 134 of the second resilient prong 130. As depicted, the one curved portion 142a of the first resilient prong 120 is configured to interlock with or engage with the two curved portions 142b, 142c of the second resilient prong 130. For example, when the distal ends 124, 134 of the first and second resilient prongs 120, 130, respectively, are displaced toward each other the engagement features 140a, 140b may interlock with each other.

Upon interlocking of the one curved portion 142a of the first resilient prong 120 and the two curved portions 142b, 142c of the second resilient prong 130, the one curved portion 142a of the first resilient prong 120 can be configured to be at least partially disposed at a position between the two curved portions 142b, 142c of the second resilient prong 130 (i.e., wherein the position comprises a gap or space between the two curved portions 142b, 142c of the engagement feature 140b).

FIG. 1C is a front view of a portion of the medical grasping device 100 of FIG. 1A. As depicted, the first resilient prong 120 comprises a concave proximal portion 126 and a convex distal portion 128. Likewise, the second resilient prong 130 comprises a concave proximal portion 136 and a convex distal portion 138. The concave proximal portions 126, 136 are concave with respect to the extension of the longitudinal axis 10 of the elongate member 110, and the concave proximal portions 126, 136 are positioned between the elongate member 110 and the convex distal portions 128, 138, respectively. The convex distal portions 128, 138 are convex with respect to the extension of the longitudinal axis 10 of the elongate member 110, and the convex distal portions 128, 138 extend from distal ends of the concave proximal portions 126, 136, respectively.

In some embodiments, the first resilient prong 120 and/or the second resilient prong 130 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 120 and/or the second resilient prong 130 may comprise an inflection point where the first resilient prong 120 and/or the second resilient prong 130 changes concavity.

In certain other embodiments, the first resilient prong may be curved (i.e., the first resilient prong may comprise a concave proximal portion and a distal convex portion); however, the second resilient prong may be substantially straight. For example, the second resilient prong may extend substantially parallel with respect to the extension of the longitudinal axis 10 of the elongate member 110 or the second resilient prong may extend, without significant curvature, at a substantially constant angle with respect to the extension of the longitudinal axis 10. The second resilient prong may also be configured to abut a luminal surface without significantly displacing and/or traumatizing the luminal surface. Such configurations of the first and second resilient prongs 120, 130 may allow or permit the substantially straight second resilient prong to be more easily displaced along or adjacent the luminal surface. Additionally, such a configuration of the first and second resilient prongs 120, 130 may allow or permit the substantially straight second resilient prong to be disposed in closer contact with the luminal surface in contrast to the curved first resilient prong which may extend away from the luminal surface. For example, if the target foreign object is closely embedded or engaged with the luminal surface, the straight resilient prong may be configured to engage or interact more easily with the target foreign object than the curved resilient prong.

In various embodiments, the medical grasping device 100 may further comprise a third resilient prong extending from the distal end 114 of the elongate member 110. Each of the first resilient prong, the second resilient prong, and the third resilient prong may extend from positions at the distal end 114 of the elongate member 110, and the positions may be substantially evenly spaced around a circumference of the elongate member 110. In various other embodiments, the medical grasping device may comprise four resilient prongs, wherein the four resilient prongs extend from the distal end 114 of the elongate member 110 and extend from positions at the distal end 114 of the elongate member 110 wherein the positions may be substantially evenly spaced around the circumference of the elongate member 110. Medical grasping devices comprising five, six, or more resilient prongs are also within the scope of this disclosure.

In some embodiments, components of the medical grasping device 100 may be integrally formed. For example, the elongate member 110 and the first and second resilient prongs 120, 130 may be integrally formed. In some other embodiments, components of the medical grasping device 100 may be discretely formed. For example, the elongate member 110 and the first and second resilient prongs 120, 130 may be discretely formed and subsequently coupled to each other.

Figure 2B:
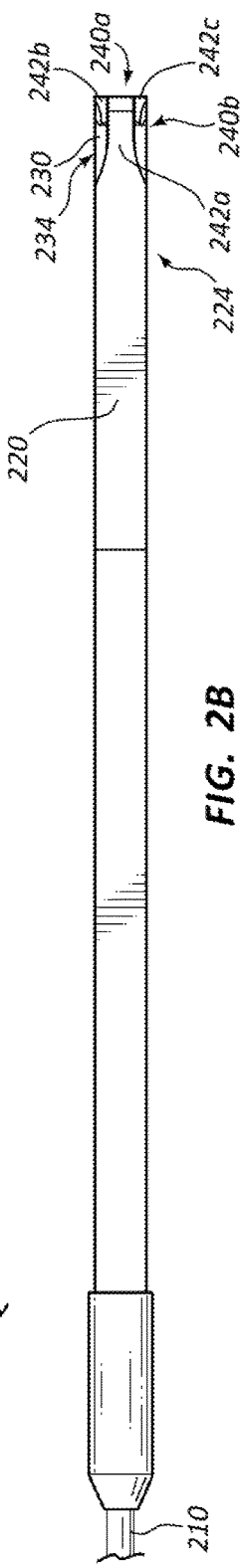
FIG. 2B is a side view of a portion of the medical grasping device of FIG. 2A.

FIGS. 2A and 2B illustrate another embodiment of a medical grasping device that can, in certain respects, resemble components of the medical grasping device described in connection with FIGS. 1A and 1B. It will be appreciated that all the illustrated embodiments may have analogous features. Accordingly, like features are designated with like reference numerals, with the leading digits incremented to "2." For instance, the elongate member is designated as "110" in FIGS. 1A and 1B, and an analogous elongate member is designated as "210" in FIGS. 2A and 2B. Relevant disclosure set forth above regarding similarly identified features thus may not be repeated hereafter. Moreover, specific features of the medical grasping device and related components shown in FIGS. 1A and 1B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the medical grasping device of FIGS. 2A and 2B. Any suitable combination of the features, and variations of the same, described with respect to the medical grasping device and components illustrated in FIGS. 1A and 1B can be employed with the medical grasping device and components of FIGS. 2A and 2B, and vice versa. This pattern of disclosure applies equally to further embodiments depicted in subsequent figures and described hereafter.

The medical grasping device 200 of FIG. 2A comprises an elongate member 210. In some embodiments, the elongate member may be configured for displacement through a body lumen (e.g., a vessel of a patient). The medical grasping device 200 further comprises a plurality of resilient prongs extending from a distal end 214 of the elongate member 210. In the illustrated embodiment, the medical grasping device 200 comprises a first resilient prong 220 and a second resilient prong 230. Further, first and second engagement features 240*a*, 240*b* are coupled to distal ends 224, 234 of each of the first and second resilient prongs 220, 230. In some embodiments, each of the first and second resilient prongs 220, 230, respectively, and the first and second engagement features 240*a*, 240*b* are configured to secure a foreign object disposed within a body lumen.

A medical grasping device assembly may comprise a delivery sheath 250 disposed around at least a portion of the medical grasping device 200, such that the medical grasping device 200 is longitudinally displaceable within the delivery sheath 250. For example, the elongate member 210 and the medical grasping device 200 may be proximally and distally displaced within a lumen 252 of the delivery sheath 250. Upon proximal displacement of the plurality of resilient prongs into the lumen 252 of the delivery sheath 250, the first and second engagement features 240*a*, 240*b* can be displaced toward each other, and upon distal displacement of the plurality of resilient prongs out of the lumen 252 of the delivery sheath 250 the first and second engagement features 240*a*, 240*b* can be displaced away from each other. Stated another way, upon proximal displacement of the plurality of resilient prongs within or into the lumen 252 of the delivery sheath 250, a constraining force may be exerted on the first and second engagement features 240*a*, 240*b*, at least in part by the delivery sheath, such that the first and second engagement features 240*a*, 240*b* are displaced or moved toward each other.

Further, upon distal displacement of the plurality of resilient prongs away from or out of the lumen 252 of the delivery sheath 250 the constraining force may be removed from the first and second engagement features 240*a*, 240*b* such that the first and second engagement features 240*a*, 240*b* displace or move away from each other. In some embodiments, partial constraint of proximal portions of resilient prongs, similar to the first and second resilient prongs 220, 230, can cause displacement or movement of engagement features, similar to the first and second engagement features 240*a*, 240*b*, toward each other.

In some embodiments, upon proximal displacement of the first and second resilient prongs 220, 230 into the lumen 252 of the delivery sheath 250, the first engagement feature 240*a* may be configured to interlock with the second engagement feature 240*b*. The interlocking of the first engagement feature 240*a* and the second engagement feature 240*b* may be configured to secure a foreign object within a body lumen.

In certain embodiments, the medical grasping device 200 may further comprise an actuator (not shown) configured to alternatively displace the plurality of resilient prongs into and/or out of the lumen 252 of the delivery sheath 250. For example, the actuator may be configured to actuate the medical grasping device 200 such that the plurality of resilient prongs and/or the engagement features may engage and/or secure a foreign object within a body lumen. In various embodiments, the actuator may be spring loaded such that upon release of the actuator by a practitioner, the plurality of resilient prongs can be disposed within the lumen 252 of the delivery sheath 250. In various other embodiments, the actuator may be spring loaded such that upon release of the actuator by a practitioner, the plurality of resilient prongs can be displaced outside and distally from within the lumen 252 of the delivery sheath 250.

In the illustrated embodiment, the first engagement feature 240*a* comprises one curved portion 242*a*, wherein the curved portion 242*a* is disposed at the distal end 224 of the first resilient prong 220. Also, the second engagement feature 240*b* comprises two curved portions 242*b*, 242*c*, wherein the curved portions 242*b*, 242*c* are disposed at the distal end 234 of the second resilient prong 230. The curved portions 242*a*, 242*b*, 242*c* of the medical grasping device 200 are generally more tapered relative to the curved portions 142*a*, 142*b*, 142*c* of the medical grasping device 100 of FIGS. 1A and 1B. For example, a distal end of the curved portion 242*a* tapers to a wedge-like configuration or shape, whereas a distal end of the curved portion 142*a* is blunt relative to the distal end of the curved portion 242*a*. Additionally, distal ends of the curved portions 242*b*, 242*c* comprise tapered outside lateral sides while distal ends of the curved portions 142*b*, 142*c* comprise tapered inside lateral sides. Other configurations or shapes of the engagement features and/or curved portions are also contemplated. For example, the configurations or shapes of the engagement features and/or the curved portions may be designed for different purposes or uses. For example, engagement features and/or curved portions comprising a first shape may be better suited for the engagement and retrieval of a stent while engagement features and/or curved portions comprising a second shape may be better suited for engagement and retrieval of a vascular filter.

With continued reference to FIG. 2A, each of the first and second engagement features 240*a*, 240*b* comprises at least one curved portion 242*a*, 242*b*, 242*c*, wherein the at least one curved portion 242*a*, 242*b*, 242*c* curves inwardly toward an extension of a longitudinal axis 10 of the elongate member 210.

FIG. 2B is a side view of a portion of the medical grasping device 200 of FIG. 2A. In the illustrated embodiment, the position of the first resilient prong 220 relative to the position of the second resilient prong 230 is shown. The first engagement feature 240*a* can be disposed at the distal end 224 of the first resilient prong 220. Likewise, the second engagement feature 240*b* can be disposed at the distal end 234 of the second resilient prong 230. Additionally, the first engagement feature 240*a* comprises one curved portion 242*a*, wherein the curved portion 242*a* is disposed at the distal end 224 of the first resilient prong 220. Also, the second engagement feature 240*b* comprises two curved portions 242*b*, 242*c*, wherein the curved portions 242*b*, 242*c* are disposed at the distal end 234 of the second resilient prong 230. As described above, the one curved portion 242*a* of the first resilient prong 220 is configured to interlock or engage with the two curved portions 242*b*, 242*c* of the second resilient prong 230 when the distal ends 224, 234 of the first and second resilient prongs 220, 230, respectively, are displaced toward each other. Upon interlocking of the one curved portion 242*a* of the first resilient prong 220 and the two curved portions 242*b*, 242*c* of the second resilient prong 230, the one curved portion 242*a* of the first resilient prong 220 can be configured to be at least partially disposed at a position (i.e., in a gap or space) between the two curved portions 242*b*, 242*c* of the second resilient prong 230.

FIG. 3A illustrates yet another embodiment of a medical grasping device 300. The medical grasping device 300 also comprises an elongate member 310. A cross-section of the elongate member 310 can be substantially circular. In some embodiments, however, the cross-section of the elongate member 310 may be substantially ovoid, square, triangular, or otherwise shaped. The medical grasping device 300 further comprises a first resilient prong 320 and a second resilient prong 330, wherein each of the first resilient prong 320 and the second resilient prong 330 is coupled to and extend from a distal end 314 of the elongate member 310.

The second resilient prong 330 of the illustrated embodiment further comprises a window or opening 331 extending longitudinally through at least a portion of the second resilient prong 330. As depicted, the first resilient prong 320 is generally narrower than the second resilient prong 330. The window 331 of the second resilient prong 330 may result in a second resilient prong 330 that comprises a substantially similar flexibility or resiliency to the flexibility or resiliency of the first resilient prong 320. The opening 331 may compensate for the greater width of the second resilient prong 330 relative to the first resilient prong 320. For example, the window 331 disposed through the wider second resilient prong 330 may generate or result in a second resilient prong 330 that comprises substantially comparable or equal amounts of material as the narrower first resilient prong 320, and as such the first and second resilient prongs 320, 330 may comprise substantially similar flexibilities or resiliencies.

A cross-section of each of the first resilient prong 320 and the second resilient prong 330 can be substantially semicircular. In some other embodiments, however, the cross-sections of the first and second resilient prongs 320, 330 may be substantially linear, L-shaped, or otherwise shaped. In some embodiments, a medical grasping device may be cut from a tube of a shape memory alloy. For example, the medical grasping device 300 may be cut from a tube of NITINOL and formed (i.e., be heat set) such that the first resilient prong 320 and the second resilient prong 330 are configured to move away from each other upon displacement of the medical grasping device out of a lumen of a delivery sheath. In some other embodiments, a medical grasping device may be milled from a block of material (i.e., a block of a metal).

FIG. 3B is a side view of the medical grasping device 300 of FIG. 3A. As illustrated, the medical grasping device 300 comprises the elongate member 310 and first and second resilient prongs 320, 330 coupled to and extending from the distal end 314 of the elongate member 310. From this view, the alignment of the first and second resilient prongs 320, 330 and their associated first and second engagement features 340*a*, 340*b*, respectively, can be seen. The first and second engagement features 340*a*, 340*b*, similar to the engagement features discussed above, can be configured to interlock with each other (i.e., via curved portions).

Figure 4E:
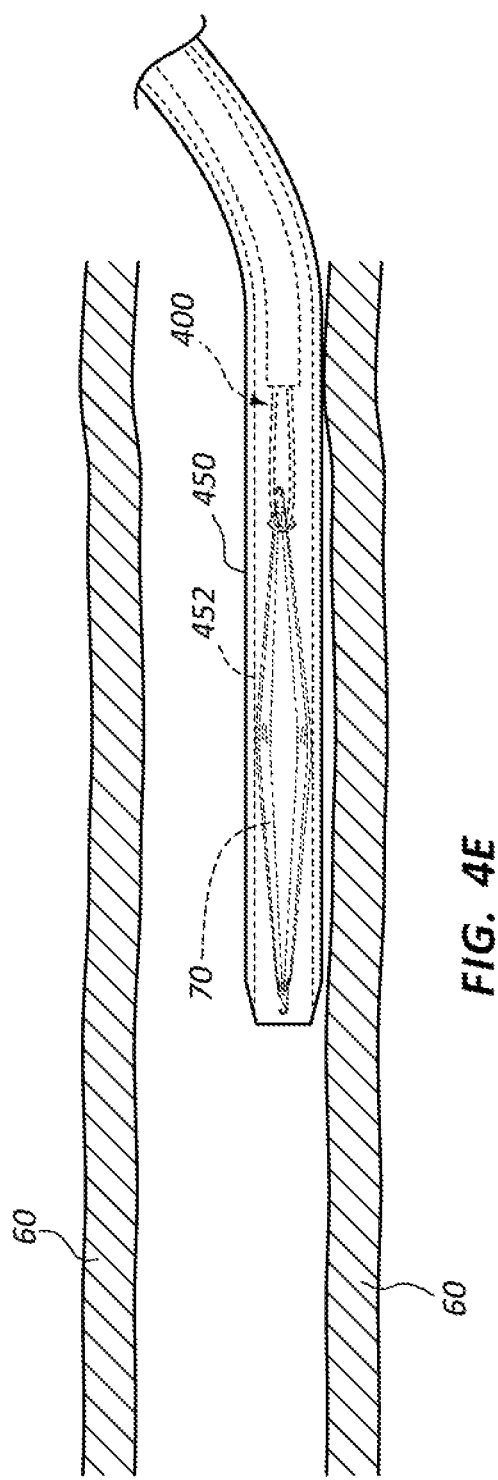
FIG. 4E is a side view of the medical grasping device assembly of FIG. 4A wherein the medical grasping device and the secured vascular filter have been disposed within the lumen of the delivery sheath.

FIGS. 4A-4E depict an illustrative method of using a medical grasping device assembly of the present disclosure to retrieve a target foreign object (e.g., a vascular filter, as illustrated) from a body lumen (e.g., a vessel as illustrated) of a patient. Although FIGS. 4A-4E depict a method of retrieving the vascular filter 70 from the vessel 60, methods of using the medical grasping device assembly of the present disclosure may also comprise methods of retrieving any target foreign object from within any body lumen. FIG. 4A is a side view of an embodiment of a medical grasping device assembly disposed with a lumen 62 of the vessel 60. The medical grasping device assembly comprises a grasping device 400, or medical grasping device, disposed within a lumen 452 of a delivery sheath 450. The method of retrieving the vascular filter 70, or the target foreign object, can comprise disposing the grasping device 400 and at least a distal end of the delivery sheath 450 to a position within the vessel 60 at or adjacent the vascular filter 70. As depicted, the grasping device 400 comprises an elongate member 410 and a plurality of resilient prongs, wherein each of the plurality of resilient prongs is coupled to and extends from a distal end 414 of the elongate member 410. Further, at least one engagement feature 440*a*, 440*b* can be disposed at distal ends 424, 434 of each of the first and second resilient prongs 420, 430, respectively. In some embodiments, as described above, the engagement features 440*a*, 440*b* may be configured to interlock to secure the vascular filter 70, or target foreign object. The target foreign object 70 can be selected from at least one of, but not limited to, a stent, a vascular filter, an embolus, or a bolus.

FIG. 4B is a side view of the medical grasping device assembly of FIG. 4A wherein the first and second resilient prongs 420, 430 of the medical grasping device 400 are at least partially distally displaced from within the lumen 452 of the delivery sheath 450. FIG. 4C is a side view of the medical grasping device assembly of FIG. 4A wherein the first and second resilient prongs 420, 430 of the medical grasping device 400 are fully displaced from within the lumen 452 of the delivery sheath 450. As depicted in FIGS. 4B and 4C, a method of retrieving the vascular filter 70, or target foreign object, can also comprise engaging at least one of the engagement features 440*a*, 440*b* with at least a portion of the vascular filter 70. For example, at least one of the engagement features 440*a*, 440*b* may contact at least a portion of the vascular filter 70 or at least one of the engagement features 440*a*, 440*b* may enter a space or volume defined by an outermost boundary of components of the vascular filter 70.

In some embodiments, a method of retrieving the target foreign object can further comprise actuating the grasping device 400 such that at least two of the engagement features 440*a*, 440*b* interlock with each other to secure the engaged target foreign object. In various embodiments, the method of retrieving the target foreign object can also comprise longitudinally displacing the grasping device 400 to dislodge or free the secured target foreign object from a position within a body lumen. For example, the grasping device may be displaced proximally toward a practitioner to dislodge the target foreign object from the body lumen. In some circumstances, tissue ingrowth may be disposed around at least a portion of the target foreign object. As used herein, the term "tissue ingrowth" refers to tissue at or adjacent a target foreign object that has grown in and/or around at least a portion of the target foreign object. The practitioner may increase a longitudinal force applied both proximally and distally upon the secured target foreign object to dislodge or free the target foreign object from the tissue ingrowth.

FIG. 4D is a side view of the medical grasping device assembly of FIG. 4A wherein the medical grasping device 400 has secured the vascular filter 70. In the illustrated embodiment, the practitioner may proximally displace the plurality of resilient prongs within the lumen 452 of the delivery sheath 450. The delivery sheath 450 can be disposed around at least a portion of the grasping device 400, and upon proximal displacement of the plurality of resilient prongs within the lumen 452 of the delivery sheath 450, an interaction between at least a portion of the delivery sheath 450 and the plurality of resilient prongs may act to displace each of the plurality of resilient prongs toward each other. Further, as depicted, the at least two engagement features 440*a*, 440*b* can interlock prior to displacement, or complete displacement, of the plurality of resilient prongs within the lumen 452 of the delivery sheath 450. The interlocking of the at least two engagement features 440*a*, 440*b* may secure the vascular filter 70 such that the vascular filter 70 may be displaced by the grasping device 400 within the lumen 452 of the delivery sheath 450. Thus, the vascular filter 70 may be secured by the medical grasping device 400 such that the vascular filter 70 is encircled by the medical grasping device 400 before a force is exerted on the vascular filter 70. This can allow or permit securement of the vascular filter 70 without, or with decreased, trauma to the vessel 60 or other body part, as the steps of securing the vascular filter 70 may be executed without displacing the vascular filter 70. In other words, the process of securing the vascular filter 70 may not disturb the placement of the vascular filter 70. In turn, this may facilitate a more controlled eventual displacement of the vascular filter 70 as the vascular filter 70 may be coupled to the medical grasping device 400 during any displacement of the vascular filter 70.

FIG. 4E is a side view of the medical grasping device assembly of FIG. 4A wherein the medical grasping device 400 and the secured vascular filter 70 have been disposed within the lumen 452 of the delivery sheath 450. As illustrated, the method can further comprise disposing the secured target foreign object 70 within the lumen 452 of the delivery sheath 450. In certain embodiments, the method may also comprise removing or retrieving each of the delivery sheath 450, the grasping device 400, and the secured target foreign object 70 from the body lumen 60 of the patient.

FIGS. 5A-5C illustrate another embodiment of a medical grasping device 500. As with the other embodiments disclosed herein, the embodiment of FIGS. 5A-5C may have analogous features to other embodiments. Disclosure set forth above with respect to these other embodiments, for example the embodiment of FIGS. 1A-1C, but thus be analogously applied to the embodiment of FIGS. 5A-5C.

FIGS. 5A and 5B illustrate an embodiment of a medical grasping device 500 in an open configuration. FIG. 5C illustrates the medical grasping device of FIGS. 5A and 5B in a closed configuration. As depicted, the medical grasping device 500 can comprise an elongate member 510. The medical grasping device 500 may also comprise at least two resilient prongs 520, 530. In the illustrated embodiment, the medical grasping device 500 comprises a first resilient prong 520 and a second resilient prong 530. In other embodiments, the medical grasping device 500 may comprise three resilient prongs, four resilient prongs, or more resilient prongs. The first and second resilient prongs 520, 530 are coupled to the elongate member 510 at a distal end 514 of the elongate member 510, and each of the first and second resilient prongs 520, 530 can extend distally from the distal end 514 of the elongate member 510.

At least one engagement feature 540a may be disposed at a distal end 524 of the first resilient prong 520. Likewise, at least one engagement feature 540b may be disposed at a distal end 534 of the second resilient prong 530. In the illustrated embodiment, the engagement feature 540a comprises one curved portion 542a, wherein the curved portion 542a is disposed at the distal end 524 of the first resilient prong 520. Also, as illustrated, the engagement feature 540b comprises two curved portions 542b, 542c, wherein the two curved portions 542b, 542c are disposed at the distal end 534 of the second resilient prong 530. The one curved portion 542a of the first resilient prong 520 may be configured to interlock or engage with the two curved portions 542b, 542c of the second resilient prong 530 when the distal ends 524, 534 of the first and second resilient prongs 520, 530, respectively, are displaced toward each other (as discussed in further detail below). The interlocking of the curved portions 542a, 542b, 542c may be configured to secure a target foreign object disposed within a body lumen. For example, a target foreign object may be secured before any force is applied on the target foreign object by a medical grasping device. Such a configuration may facilitate a traumatic, or less traumatic, securement of the target foreign object prior to displacement of the target foreign object.

With comparison to the embodiment of FIGS. 1A-1C, the medical grasping device 500 of FIGS. 5A-5C, the curved portion 542 a further comprises a distal lip 542 a'. The distal lip 542 a' may be configured to contact with an interior portion distal portion 534 of the second resilient prong 530. As shown in FIG. 5C, contact between the distal lip 542 a' and the distal portion 534 of the second resilient prong 530 may provide a positive stop for relative displacement between the first resilient arm 520 and the second resilient arm 530. This positive stop may prevent over extension of the first resilient prong 520 and second resilient prong 530 and/or may prevent the curved portion 542 a from passing through the two curved portions 542 b, 542 c of the second resilient prong 530 and catching on an exterior surface of the second resilient prong 530.

As discussed above, the first resilient prong 520 and second resilient prong 530 may be constrained within the sheath or catheter when in a closed configuration, such as that of FIG. 5C. When in such a closed configuration, constraints on the curved resilient prongs 520, 530 may thus result in a grasping or closing force acting on the resilient prongs 520, 530. The positive stop provided by the distal lip 542a' may prevent the distal ends of the resilient prongs 520, 530 from over-extension, such as by preventing the distal ends of the resilient prongs 520, 530 from crossing each other. This may, in turn, prevent the resilient prongs 520, 530 from catching in a closed position, for example, by preventing the first engagement feature 542a from snapping past the second resilient prong 530 and engagement with an exterior surface of the second resilient prong 530. Such engagement could potentially prevent the medical grasping device 500 from reopening once the constraining force is removed.

Also as compared to the embodiment of FIGS. 1A-1C, the first resilient prong 520 and the second resilient prong 530 may comprise a different curvature. Various scales, sizes, and curvatures of resilient prongs are within the scope of this disclosure. As with other embodiments disclosed herein, the first resilient prong 520 and the second resilient prong 530 may be laser cut from a single piece of material or may be stamped from a single material and coupled together with a collar or other coupling member.

With reference to FIG. 5A, each of the first resilient prong 520 and the second resilient prong 530 curves outwardly from an extension of a longitudinal axis 12 of the elongate member 510. In contrast, each of the curved portions 542a, 542b, 542c curves inwardly toward the extension of the longitudinal axis 12 of the elongate member 510. Again, this shape and curvature may differ from other embodiments, such as the embodiment of FIGS. 1A-1C.

As depicted, each of the first resilient prong 520 and the second resilient prong 530 extends from the distal end 514 of the elongate member 510 such that the first resilient prong 520 extends in a substantially opposite direction from the second resilient prong 530. Stated another way, the extension of the first resilient prong 520 from the elongate member 510 generates or forms a substantially mirror image of the extension of the second resilient prong 530 from the elongate member 510, and vice versa. As illustrated, the first resilient prong 520 extends from a first portion at the distal end 514 of the elongate member 510 and the second resilient prong 530 extends from a second portion at the distal end 514 of the elongate member 510, wherein the first position and the second position are disposed at substantially opposite positions along a circumference of the distal end 514 of the elongate member 510. As such, each of the first resilient prong 520 and the second resilient prong 530 is substantially disposed within a single plane. Other dispositions of the first and second resilient prongs 520, 530 around the circumference of the distal end 514 of the elongate member are also within the scope of this disclosure.

FIG. 5B is a side view of a portion of the medical grasping device 500 of FIG. 5A, with the medical grasping device disposed in an open configuration as in FIG. 5A. In the illustrated embodiment, the relative position of the first resilient prong 520 in relation to the position of the second resilient prong 530 is shown. As described above, at least one engagement feature 540a can be disposed at the distal end 524 of the first resilient prong 520. Likewise, at least one engagement feature 540b may be disposed at the distal end 534 of the second resilient prong 530. The engagement feature 540a of the first resilient prong 520, as illustrated, comprises one curved portion 542a, wherein the curved portion 542a is disposed at the distal end 524 of the first resilient prong 520. The engagement feature 540b of the second resilient prong 530 comprises two curved portions 542b, 542c, wherein the curved portions 542b, 542c are disposed at the distal end 534 of the second resilient prong 530. The distal lip 542a' of the curved portion 542a of the first resilient prong 520 is also shown. As depicted, the one curved portion 542a of the first resilient prong 520 is configured to interlock with or engage with the two curved portions 542b, 542c of the second resilient prong 530. For example, when the distal ends 524, 534 of the first and second resilient prongs 520, 530, respectively, are displaced toward each other the engagement features 540a, 540b may interlock with each other. The distal lip 542a' may provide a positive stop as described above.

Upon interlocking of the one curved portion 542a of the first resilient prong 520 and the two curved portions 542b, 542c of the second resilient prong 530, the one curved portion 542a of the first resilient prong 520 can be configured to be at least partially disposed at a position between the two curved portions 542b, 542c of the second resilient prong 530 (i.e., wherein the position comprises a gap or space between the two curved portions 542b, 542c of the engagement feature 540b). Again, the distal lip 542a' may provide a positive stop though interaction with the second resilient prong 530, preventing over-extension of the first resilient prong 520 and second resilient prong 530 with respect to each other.

FIG. 5C is a front view of a portion of the medical grasping device 500 of FIG. 5A, with the first resilient prong 520 and the second resilient prong 530 disposed in a closed configuration. As depicted, the first resilient prong 520 comprises a concave proximal portion 526 and a convex distal portion 528. Likewise, the second resilient prong 530 comprises a concave proximal portion 536 and a convex distal portion 538. The concave proximal portions 526, 536 are concave with respect to the extension of the longitudinal axis 12 of the elongate member 510, and the concave proximal portions 526, 536 are positioned between the elongate member 510 and the convex distal portions 528, 538, respectively. The convex distal portions 528, 538 are convex with respect to the extension of the longitudinal axis 12 of the elongate member 510, and the convex distal portions 528, 538 extend from distal ends of the concave proximal portions 526, 536, respectively. As discussed above, in this closed configuration the distal lip 542a' is in contact with an interior surface of the distal portion 534 of the second resilient prong 530. This contact may provide a positive stop and may aid in preventing the first resilient prong 520 and second resilient prongs 530 from crossing each other when the medical grasping device 500 is constrained in a closed configuration.

In some embodiments, the first resilient prong 520 and/or the second resilient prong 530 may comprise a first curve centered on a point outside of the first curve and a second curve centered on a point inside of the second curve. The radius of the first curve may be different from the radius of the second curve. Additionally, the first curve and the second curve may comprise a constant and/or a changing radius of curvature. In various embodiments, the first resilient prong 520 and/or the second resilient prong 530 may comprise an inflection point where the first resilient prong 520 and/or the second resilient prong 530 changes concavity.

In certain other embodiments, the first resilient prong may be curved (i.e., the first resilient prong may comprise a concave proximal portion and a distal convex portion); however, the second resilient prong may be substantially straight. For example, the second resilient prong may extend substantially parallel with respect to the extension of the longitudinal axis 12 of the elongate member 110 or the second resilient prong may extend, without significant curvature, at a substantially constant angle with respect to the extension of the longitudinal axis 12. The second resilient prong may also be configured to abut a luminal surface without significantly displacing and/or traumatizing the luminal surface. Such configurations of the first and second resilient prongs 520, 530 may allow or permit the substantially straight second resilient prong to be more easily displaced along or adjacent the luminal surface. Additionally, such a configuration of the first and second resilient prongs 520, 530 may allow or permit the substantially straight second resilient prong to be disposed in closer contact with the luminal surface in contrast to the curved first resilient prong which may extend away from the luminal surface. For example, if the target foreign object is closely embedded or engaged with the luminal surface, the straight resilient prong may be configured to engage or interact more easily with the target foreign object than the curved resilient prong.

In various embodiments, the medical grasping device 500 may further comprise a third resilient prong extending from the distal end 514 of the elongate member 510. Each of the first resilient prong, the second resilient prong, and the third resilient prong may extend from positions at the distal end 514 of the elongate member 510, and the positions may be substantially evenly spaced around a circumference of the elongate member 510. In various other embodiments, the medical grasping device may comprise four resilient prongs, wherein the four resilient prongs extend from the distal end 514 of the elongate member 510 and extend from positions at the distal end 514 of the elongate member 510 wherein the positions may be substantially evenly spaced around the circumference of the elongate member 510. Medical grasping devices comprising five, six, or more resilient prongs are also within the scope of this disclosure.

Again, as discussed above, in some embodiments, components of the medical grasping device 500 may be integrally formed. For example, the elongate member 510 and the first and second resilient prongs 520, 530 may be integrally formed. In some other embodiments, components of the medical grasping device 500 may be discretely formed. For example, the elongate member 510 and the first and second resilient prongs 520, 530 may be discretely formed and subsequently coupled to each other.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A medical grasping device for use in an interventional procedure in a body lumen of a patient, comprising:
    an elongate member;
    a first resilient prong extending from a distal end of the elongate member, the first resilient prong comprising a first engagement feature having a first curved portion disposed at a distal end of the first resilient prong; and
    a second resilient prong extending from the distal end of the elongate member, the second resilient prong comprising a second engagement feature having a second curved portion and a third curved portion disposed at a distal end of the second resilient prong, wherein the first curved portion is configured to interlock with the second and third curved portions when the first and second resilient prongs are displaced toward each other,
    wherein each curved portion curves inwardly toward an extension of a longitudinal axis of the elongate member and further curves toward a proximal direction, and
    wherein the first curved portion comprises a distal lip extending from the first curved portion and configured to engage with an interior surface of the second engagement feature at a location proximal of the second and third curved portions when the medical grasping device is disposed in a closed configuration.

2. The medical grasping device of claim 1, wherein each of the first resilient prong and the second resilient prong curves outwardly from the extension of the longitudinal axis of the elongate member, and wherein each of the first resilient prong and the second resilient prong curves inwardly toward the extension of the longitudinal axis of the elongate member.

3. The medical grasping device of claim 1, wherein upon interlocking of the first curved portion of the first engagement feature and the second and third curved portions of the second engagement feature the first curved portion of the first engagement feature is configured to be disposed laterally at a position between the second and third curved portions of the second engagement feature.

4. The medical grasping device of claim 1, wherein a cross-section of the elongate member is substantially circular, and wherein cross-sections of each of the first and second resilient prongs are substantially semicircular.

5. The medical grasping device of claim 1, wherein each of the first resilient prong and the second resilient prong comprises a concave proximal portion and a convex distal portion, wherein the concave proximal portion is concave with respect to the extension of the longitudinal axis of the elongate member, wherein the concave proximal portion is positioned between the elongate member and the convex distal portion, wherein the convex distal portion is convex with respect to the extension of the longitudinal axis of the elongate member and wherein the convex distal portion extends from a distal end of the concave proximal portion.

6. The medical grasping device of claim 1, wherein the medical grasping device is configured to be disposed within a lumen of a delivery sheath.

7. The medical grasping device of claim 6, wherein the first and second resilient prongs are configured to be longitudinally displaced from a position within the lumen of the delivery sheath to a position distal to the delivery sheath, and wherein the first and second resilient prongs are further configured to be longitudinally displaced from the position distal to the delivery sheath to the position within the lumen of the delivery sheath.

8. The medical grasping device of claim 1, wherein the first resilient prong is curved and wherein the second resilient prong is substantially straight such that the second resilient prong extends substantially parallel with respect to the extension of a longitudinal axis of the elongate member.

9. The medical grasping device of claim 1, wherein the medical grasping device is cut from a tube of a shape memory alloy.

10. The medical grasping device of claim 1, wherein the first curved portion disposed at the distal end of the first resilient prong and the second and third curved portions disposed at the distal end of the second resilient prong at least partially laterally overlap when the medical grasping device is disposed in the closed configuration.

11. The medical grasping device of claim 1, wherein the distal lip comprises a positive stop, wherein the positive stop is configured to engage the second engagement feature between the second and third curved portions when the medical grasping device is in the closed configuration.

12. A medical device for retrieving a foreign object from a body lumen, the medical device comprising:
    an elongate member configured for displacement through a body lumen; and a plurality of resilient prongs extending from a distal end of the elongate member,
    wherein at least one engagement feature is coupled to a distal end of each resilient prong,
    wherein each of the resilient prongs and the engagement features are configured to secure a foreign object disposed within the body lumen,
    wherein at least two of the engagement features comprise at least one curved portion,
    wherein at least two engagement features are configured to interlock with each other,
    wherein at least one curved portion of one engagement feature at least partially laterally overlaps at least one curved portion of another engagement feature when the medical device is disposed in a closed configuration,
    wherein at least one curved portion of one engagement feature comprises a distal lip extending from the at least one curved portion and configured to engage an interior surface of another engagement feature when the medical device is disposed in a closed configuration, and
    wherein the interior surface is located proximal to the at least one curved portion of the another engagement surface.

13. The medical device of claim 12, further comprising:
    a delivery sheath disposed around at least a portion of the medical device such that the medical device is longitudinally displaceable within the delivery sheath, wherein upon proximal displacement of the plurality of resilient prongs into a lumen of the delivery sheath the engagement features are displaced toward each other, and wherein upon distal displacement of the plurality of resilient prongs out of the lumen of the delivery sheath the engagement features are displaced away from each other.

14. The medical device of claim 13, wherein the medical device comprises a first resilient prong and a second resilient prong, wherein the first resilient prong is coupled to a first engagement feature, and wherein the second resilient prong is coupled to a second engagement feature.

15. The medical device of claim 14, wherein upon the proximal displacement of the first and second resilient prongs into the lumen of the delivery sheath the first engagement feature is configured to interlock with the second engagement feature.

16. A method of retrieving a foreign object from a body lumen, comprising:
   disposing a grasping device to a position within a body lumen adjacent a target foreign object, wherein the grasping device comprises:
      an elongate member; and
      a plurality of resilient prongs extending from a distal end of the elongate member,
         wherein at least one engagement feature is disposed at a distal end of each of the resilient prongs,
         wherein at least two of the engagement features comprise at least one curved portion,
         wherein at least one of the at least one curved portions comprises an end portion extending in an inwardly proximal direction,
         wherein at least two engagement features are configured to interlock with each other,
         wherein at least one of the at least one curved portions of one of the engagement features comprises a distal lip extending from the at least one curved portion and configured to engage an internal surface of another engagement feature, and
         wherein the internal surface is located proximally of the at least one curved portion of the another engagement feature of the plurality of resilient prongs;
   actuating the grasping device such that at least two of the engagement features interlock with each other to secure an engaged target foreign object; and
   longitudinally displacing the grasping device to dislodge the engaged target foreign object from a position within the body lumen.

17. The method of claim 16, wherein the at least two engagement features interlock prior to displacement of the plurality of resilient prongs within a lumen of a delivery sheath.

18. The method of claim 16, further comprising longitudinally displacing the grasping device to a position within a lumen of a delivery sheath,
   wherein at least one resilient prong of the plurality of resilient prongs comprises a convex portion with respect to an extension of a longitudinal axis of the elongate member, and
   wherein the convex portion is deflected toward a less convex state when the medical grasping device is disposed within the lumen of the delivery sheath.

* * * * *